(12) United States Patent
Armitage et al.

(10) Patent No.: US 7,816,106 B2
(45) Date of Patent: Oct. 19, 2010

(54) MANUFACTURE OF AMIDES

(75) Inventors: Yvonne Armitage, Holmfirth (GB); Jatinder Singh Kullar, Bradford (GB)

(73) Assignee: Ciba Specialty Chemicals Water Treatments Ltd., Bradford (GB)

( * ) Notice: Subject to any disclaimer, the term of this patent is extended or adjusted under 35 U.S.C. 154(b) by 237 days.

(21) Appl. No.: 10/580,446

(22) PCT Filed: Nov. 22, 2004

(86) PCT No.: PCT/EP2004/013253

§ 371 (c)(1),
(2), (4) Date: May 23, 2006

(87) PCT Pub. No.: WO2005/054489

PCT Pub. Date: Jun. 16, 2005

(65) Prior Publication Data

US 2007/0077633 A1    Apr. 5, 2007

(30) Foreign Application Priority Data

Dec. 2, 2003 (GB) .................... 0327906.4
Oct. 21, 2004 (GB) .................... 0423342.5

(51) Int. Cl.
*C12P 13/02* (2006.01)
*C12P 1/04* (2006.01)
*C12N 1/04* (2006.01)
*C12N 1/20* (2006.01)
*C12N 1/00* (2006.01)

(52) U.S. Cl. .................... 435/129; 435/170; 435/252.2; 435/260; 435/822

(58) Field of Classification Search .................... None
See application file for complete search history.

(56) References Cited

U.S. PATENT DOCUMENTS

| 4,900,672 | A | 2/1990 | Yamada et al. ............... 435/188 |
| 4,931,391 | A | 6/1990 | Enomoto et al. ............. 435/188 |
| 5,089,411 | A | 2/1992 | Yamada et al. ............... 435/244 |
| 5,563,053 | A | 10/1996 | Takashima et al. .......... 435/122 |
| 5,567,608 | A | 10/1996 | Doi et al. .................... 435/182 |
| 5,705,382 | A | 1/1998 | Endo et al. .................. 435/260 |
| 5,827,699 | A | 10/1998 | Yanenko et al. ............. 435/129 |
| 5,998,180 | A | 12/1999 | Armitage et al. ............ 435/138 |
| 6,043,061 | A | 3/2000 | Ishii et al. ................... 435/129 |
| 6,251,646 | B1 | 6/2001 | Dicosimo et al. ............ 435/183 |
| 6,368,804 | B1 | 4/2002 | Ben-Bassat et al. ............ 435/6 |
| 6,395,467 | B1 * | 5/2002 | Fahy et al. .................... 435/1.3 |
| 2004/0048348 | A1 | 3/2004 | Murao et al. ................ 435/170 |

FOREIGN PATENT DOCUMENTS

| EP | 0 243 966 | 11/1987 |
| EP | 0 307 926 | 3/1989 |
| JP | 2003-144144 | 5/2003 |

OTHER PUBLICATIONS

Martinkova et al.; biocatalysis and Biotransformation, vol. 20, No. 2, (2002), pp. 73-93.
Mylerova et al.; Current Organic Chemistry, vol. 7, (9/03), pp. 1279-1295.
Kaufmann et al., Steroids vol. 64 (1999) pp. 535-540.
T. Nagasawa et al.; Appl. Microbiol Biotechnol vol. 34: pp. 783-788 (1991).
T. Nagasawa et al.; Pure & Appl. Chem. vol. 67, No. 7, pp. 1241-1256 (1995).
T. Leonova et al.; Applied Biochemistry and Biotechnology, vol. 88, (2000), pp. 231-241.
A. Yanenko et al., Proceedings of the Ninth Symposium on the Actinomycetes, (1995), pp. 139-144.
T. Nagasawa et al., Eur. J. Biochem. Vol. 196, pp. 581-589 (1991).
Page 47, of Enzyme preparation and use, Chaplin & Bucke (1990), Cambridge University Press.
Patent Abstracts of Japan Pub. No. 2003144144.

* cited by examiner

*Primary Examiner*—Vera Afremova
(74) *Attorney, Agent, or Firm*—Shiela A. Loggins

(57) ABSTRACT

A method of producing an amide from the corresponding nitrile comprising the following steps, i) providing a microorganism capable of producing a nitrile hydratase biocatalyst, ii) culturing the microorganism in a growth medium, iii) storing the microorganism, iv) contacting the nitrile by the microorganism in an aqueous medium and thereby converting the nitrile to the amide, wherein the microorganism is stored as none actively growing free cells in a storage medium that comprises water. The stored microorganism may be as whole microbial cells, this may be in the form of a cell paste recovered from a fermentation medium; an aqueous suspension of the microbial cells, prepared using a suitable suspending medium such as water, physiological saline solution, or a suitable buffer solution, such as phosphate or comprises the fermentation broth that contains components of the fermentation culture medium and products of microbial culture. The microorganism exhibits no significant loss of activity, for example if stored even for at least 2 days, especially 3 to 28 days.

5 Claims, No Drawings

MANUFACTURE OF AMIDES

The present invention relates to a method for the manufacture of amides from the corresponding nitrile using a biocatalyst that is a microorganism capable of producing a nitrile hydratase enzyme.

It is well known to employ biocatalysts, such as microorganisms that contain enzymes, for conducting chemical reactions. Nitrile hydratase enzymes are known to catalyse the hydration of nitrites directly to the corresponding amides. Typically nitrile hydratase enzymes can be produced by a variety of microorganisms, for instance microorganisms of the genus *Bacillus, Bacteridium, Micrococcus, Brevibacterium, Corynebacterium, Pseudomonas, Acinetobacter, Xanthobacter, Streptomyces, Rhizobium, Klebsiella, Enterobacter, Erwinia, Aeromonas, Citrobacter, Achromobacter, Agrobacterium, Pseudonocardia* and *Rhodococcus*.

Various strains of the *Rhodococcus rhodochrous* species have been found to very effectively produce nitrile hydratase enzyme. EP-0 307 926 describes the culturing of *Rhodococcus rhodochrous*, specifically strain J1 in a culture medium that contains cobalt ions. The nitrile hydratase can be used to hydrate nitrites into amides, and in particular the conversion of 3-cyanopyridine to nicotinamide. *Rhodococcus rhodochrous* J1, is used commercially to manufacture acrylamide monomer from acrylonitrile and this process has been described by Nagasawa and Yamada Pure Appl. Chem. 67: 1241-1256 (1995). EP-A-0362829 describes a method for cultivating bacteria of the species *Rhodococcus rhodochrous* comprising at least one of urea and cobalt ion for preparing the cells of *Rhodococcus rhodochrous* having nitrile hydratase activity. Specifically described is *Rhodococcus rhodochrous* J1.

Leonova et al., Appl. Biochem. Biotechnol. 88: 231-241 (2000) entitled, "Nitrile Hydratase of *Rhodococcus*", describes the growth and synthesis of nitrile hydratase in *Rhodococcus rhodochrous* M8. The nitrile hydratase synthesis of this strain is induced by urea in the medium, which is also used as a nitrogen source for growth by this organism. Cobalt is also required for high nitrile hydratase activity. This literature paper looks at induction and metabolic effects in the main.

Leonova et al., Appl. Biochem. Biotechnol. 88: 231-241 (2000) also states that acrylamide is produced commercially in Russia using *Rhodococcus rhodochrous* M8. Russian patent 1731814 describes *Rhodococcus rhodochrous* strain M8.

*Rhodococcus rhodochrous* strain M33 that produces nitrile hydratase without the need of an inducer such as urea is described in U.S. Pat. No. 5,827,699. This strain of microorganism is a derivative of *Rhodococcus rhodochrous* M8.

A major disadvantage with the use of biocatalysts is the general lack of stability observed with wet microbial material during storage, transportation and use. Even with relatively stable enzymes and bacteria such as nitrile hydratases in Rhodococcal cells, the potential for spoilage before use has led to acceptance within the industry for the need to process the biocatalyst cell suspension in some way e.g. by freezing or freeze-drying of the aqueous mixture or alternatively immobilisation of the cells in some polymer matrix. In order to achieve maximum productivity from the biocatalyst it is important that the maximum biocatalytic activity is retained during its preparation and storage prior to use. In Chaplin and Bucke (1990) In: Enzyme Technology, published by Cambridge University Press, p 47 (Enzyme preparation and use) it was recognised that enzyme inactivation can be caused by heat, proteolysis, sub optimal pH, oxidation denaturants and irreversible inhibitors. A number of substances may cause a reduction in the rate of an enzymes ability to catalyse a reaction. This includes substances that are non-specific protein denaturants.such as urea.

In the presentation, Protein Stability, by Willem JH van Berkel, Wageningen University, factors that may cause protein deactivation or unfolding were considered and these included proteases, oxidation due to the presence of oxygen or oxygen radicals and denaturing agents causing reversible unfolding. such as urea.

Chaplin and Bucke (1990) In Enzyme Technology, published by Cambridge University Press, p 73 (Enzyme preparation and use) revealed that the key factor regarding the preservation of enzyme activity involves maintaining the conformation of the enzyme structure. Therefore it was considering important to prevent unfolding, aggregation and changes in the covalent structure. Three approaches for achieving this were considered: (1) use of additives; (2) the controlled use of covalent modification; and (3) enzyme immobilisation.

EP-B-0-243-967 describes the preservation of nitrile hydration activity of nitrilase by the addition of stabilizing compounds selected from nitrites, amides and organic acids and their salts to a solution or suspension of the enzyme, or the immobilized form of the enzyme. It clearly states in the description that while a solution or suspension of a microorganism capable of producing nitrilase that hydrates nitriles such as acrylonitrile, to produce the corresponding amides such as acrylamide may be stored at room temperature as long as the storage period is short, storage at a low temperature, especially at a temperature in the vicinity of 0° C. is preferred. It was described in EP-A-0 707 061 that addition of inorganic salts at a concentration of between 100 mM to the saturation concentration of the inorganic salts to an aqueous medium containing either a suspension of microbial cells or immobilized microbial cells preserved the cells and enzyme activity for a prolonged period of time. This technique is described for the preservation of microbial cells that have nitrile hydratase or nitrilase activity. The addition of bicarbonate or carbonate salts to an aqueous solution of immobilised or unimmobilised microbial cells having nitrilase activity is described in U.S. Pat. No. 6,368,804. Immobilisation has frequently involved removal of the enzyme from the whole cell, before immobilising the enzyme in a matrix. However, although such immobilisation provides very good protection for the enzyme, extraction of the enzyme from the whole cell is an intricate step, which can be time-consuming, expensive and can lead to loss of enzyme. Additionally whole microbial cells can be immobilized. U.S. Pat. No. 5,567,608 provides a process of immobilising whole cell biocatalyst in a cationic copolymer which has good storage stability and prevents putrefaction.

*Rhodococcus rhodochrous* J1, which is used commercially to manufacture acrylamide monomer, is immobilised to (a) allow transportation and (b) to increase the longevity of the biocatalyst in use. In U.S. Pat. No. 5,567,608 the inventors state that biocatalysts are normally immobilized for use on an industrial scale, to facilitate ease of separation of the biocatalyst from the reaction product, preventing impurities from the biocatalyst eluting into the product and to assist in continuous processes and recycling of the biocatalyst. However, immobilisation is an extra processing step that requires an additional plant and the use of potentially a number of other raw materials such as alginate, carrageenan, acrylamide and other acrylate monomers, and vinyl alcohol. Thus, this is an expensive processing step.

Various other ways have been proposed for minimising the deleterious effects of enzyme inactivation in an attempt reduce the negative impact on a chemical reaction process.

In U.S. Pat. No. 6,043,061 it was revealed that the reduction of hydrocyanic acid concentration in the reaction mixture can suppress the deactivation of nitrile hydratase.

It is also known to freeze dry biocatalysts in order to preserve the activity of an enzyme in storage over prolonged period of time. Again this is a potentially expensive processing step that is normally carried out with biocatalysts prepared on a small scale. Cryopreservation in liquid nitrogen or in the vapour phase of liquid nitrogen also affords long-term storage of microbial cells but requires a constant supply of liquid nitrogen.

Growth of a microorganism for use as a biocatalyst may take place over a period of several days. During this time the microorganism is actively growing and is maintained in a state of growth by the feeding of appropriate nutrients and maintaining a correct temperature and pH for growth and supplying oxygen if required.

Normally the growth of microorganisms is limited either by the exhaustion of nutrient or the accumulation of toxic products of metabolism and the growth rate reduces. Growth is maintained by feeding appropriate nutrients and maintaining a correct temperature and pH for growth and where required supplying oxygen.

There are instances where the biocatalyst in the form of whole microbial cells has ceased its growth period but it is required to continue metabolizing for it to be an active biocatalyst, for instance for co-factor regeneration for a biocatalysed reaction to occur. In these cases compounds are fed to the biocatalyst to maintain the metabolism.

However, if a biocatalyst, such as one that produces nitrile hydratase is to be stored without continued growth for a period of time, even for a few days it is normal to remove the microbial cells from the fermentation broth, whether it is an enzyme within the cells that are required as the catalyst, or whether the enzyme is secreted into the fermentation medium. This is to prevent microbial growth in the fermentation broth causing putrefaction of the broth and to reduce protease activity that can cause the breakdown of the enzyme that is required. It is normal therefore to preserve the fermentation broth per se or to remove the cells to prevent the degradation of the biocatalyst through extraneous biological activity such as microbial contamination. The biocatalytic activity could normally be expected to reduce in a very short period of time such as within a day and certainly in less than two days if this were not carried out. Methods of preserving the activity during the storage of biocatalysts, even for periods of time up to one-week, have normally involved removal of the biocatalyst from the fermentation broth and/or immobilisation of the biocatalyst in a suitable matrix and/or stabilisation using stabilising substances which then either become contaminants in the reaction mixture and this may be a problem further downstream or an additional processing step is required to remove them from the microbial cell suspension before it is used as a biocatalyst.

In the absence of such preservation treatments biocatalysts when kept at ambient temperatures tend to lose activity to the extent that they are no longer as effective or even suitable for catalysing reactions.

It would be desirable to provide a simplified means for biologically converting nitriles to amides. Furthermore it would be desirable to store microorganisms prior to their use in the manufacture of amides without any significant loss of activity and in a way that avoids the additional processing steps normally required to achieve storage stability. It would also be desirable to avoid putrefaction of the microorganism on storage at ambient temperatures.

According to the present invention we provide a method of producing an amide from the corresponding nitrile comprising the following steps,
i) providing a microorganism capable of producing a nitrile hydratase biocatalyst,
ii) culturing the microorganism in a suitable growth medium,
iii) storing the microorganism,
iv) contacting the nitrile by the microorganism in an aqueous medium and thereby converting the nitrile to the amide, wherein the microorganism is stored as none actively growing free cells in a storage medium that comprises water.

The stored microorganism may exist as whole microbial cells, and this may be in the form of a cell paste recovered from a fermentation medium (culture medium or growth medium).

Furthermore, the microorganism may be recovered from the growth medium and then stored as an aqueous suspension of microbial cells in a suspending medium. This can for instance be an aqueous suspension of the microbial cells, prepared using a suitable suspending medium such as water, physiological saline solution or a suitable pH buffer solution, such as phosphate or the fermentation broth, that contains components of the fermentation culture medium and/or products of microbial growth.

Preferably, the microorganism is not recovered from the original fermentation medium and is stored without further downstream processing steps, such as recovery of the microorganism using for instance centrifugation or filtration.

The microbial cells may be regarded as a non-actively growing culture. By this we mean that the medium and the storage conditions in which the microorganism is held would not be expected to promote growth. The storage medium can for instance be the microbial cells recovered from the fermentation medium; water; physiological saline solution; a suitable buffer solution such as phosphate buffer or any other similar buffer or a growth medium where metabolism in the microorganism cells is substantially zero as determined by measuring the growth rate, or the biomass concentration or oxygen consumption or nutrient consumption, or other form of measurement generally used to monitor microbial growth and metabolism.

The composition or the storage medium may comprise any residual fermentation broth components. The fermentation broth may include any of the typical ingredients used for culturing the microorganism and also may include products and by-products produced by the microorganism. Typical components of the fermentation broth include sugars, polysaccharides, proteins, peptides, amino acids, nitrogen sources, inorganic salts, vitamins, growth regulators and enzyme inducers. Specifically this could include monosaccharides or disaccharides as sugars; ammonium salts or other nitrogen sources; inorganic salts such as phosphates, sulphates, magnesium, calcium, sodium and potassium salts; metal compounds; vitamins; and complex fermentation medium components, for example corn steep liquor; peptone; yeast extract; organic or inorganic compounds that may be used for specific microbial growth requirements; specific enzyme inducers (such as urea that is used to induce the nitrile hydratase of some microorganisms); and organic acids such as citrate or pyruvate; and any other organic or inorganic compounds that may be required to ensure successful growth of the microorganism.

Usually when a microorganism, such as one that produces nitrile hydratase, is stored without continued growth for a period of time, even for a few days, it is normal to remove the microbial cells from the fermentation broth, whether it is the cells that are required as the catalyst, or whether the enzyme is recovered from the cells or fermentation medium. This is to prevent microbial growth in the fermentation broth causing putrefaction of the broth and to reduce protease activity that can cause the breakdown of the enzyme that is required. It is normal therefore to preserve the fermentation broth per se or to remove the cells to prevent the degradation of the biocatalyst through extraneous biological activity such as microbial contamination. The biocatalytic activity could normally be expected to reduce in a very short period of time such as within a day and certainly in less than two days if this were not carried out.

The storage method described in this context should promote effective stability such that the biocatalyst can be readily used without any significant loss in activity. Storage stability is achieved without the necessity of resorting to for instance immobilisation, the addition of stabilising compounds, freeze drying. Storage stability may be achieved without resorting to removal of any of the fermentation broth components such as urea or urea derivatives, even though urea is a known protein deactivator.

The composition or the environment used in the method of storage may contain oxygen or can be a substantially oxygen free environment. By oxygen free we mean that the concentration of oxygen should be less than 1% dissolved oxygen concentration Removal of oxygen from the fermentation broth can be achieved by any of the conventional methods for removing oxygen. These include purging for a period of time with an inert gas, removal of any head-space in the storage container, storing under diminished pressure or the addition of known oxygen scavengers such as ascorbic acid or hydrazine and hydrazide.

It would have been expected that after 2 days and especially after several days storage there would be some loss in nitrile hydratase activity. This would have been expected even in the absence of oxygen. It would have been expected especially in the presence of residual fermentation broth components such as urea, and also at temperatures of above 0° C. This is because protease enzymes in the biocatalyst might be expected to break down other proteins in the cell, including the nitrile hydratase. However, the biocatalyst suffers none of the expected disadvantages and thus suffers no significant loss in nitrile hydratase activity.

On the contrary we find that during the storage period the activity of the biocatalyst comprising nitrile hydratase actually increases. Thus in another aspect of the invention we provide a method of increasing the nitrile hydratase activity of a biocatalyst capable of forming nitrile hydratase by storing the biocatalyst in a storage medium in accordance with the storage method of the present invention. Therefore, the method can result in a new biocatalyst composition by virtue of its increased activity. Therefore, nitrile hydratase of the biocatalyst composition, and in particular formed during storage of the biocatalyst is new. Also, the biocatalyst does not produce the mal odours associated with putrefaction during the storage period.

Preferably the storage method allows the biocatalyst to be stored for at least two days and more preferably one or more weeks. In particular the biocatalyst may be stored from 3 to 28 days, for example 3 to 14 days.

Urea or a urea derivative could be present in the biocatalyst composition through its inclusion in the fermentation mixture. In one form of the invention the composition or storage medium containing the biocatalyst may be deoxygenated and contain fermentation broth components such as urea. The biocatalyst is desirably a microorganism which is capable of generating nitrile hydratase enzyme. For instance this could be a microorganism selected from the genus *Bacillus, Bacteridium, Micrococcus, Brevibacterium, Corynebacterium, Pseudomonas, Acinetobacter, Xanthobacter, Streptomyces, Rhizobium, Klebsiella, Enterobacter, Erwinia, Aeromonas, Citrobacter, Achromobacter, Agrobacterium, Pseudonocardia* and *Rhodococcus*. The biocatalyst is especially a microorganism of the *Rhodococcus* genus, preferably of the *Rhodococcus rhodochrous* species. A particularly suitable biocatalyst is *Rhodococcus rhodochrous rhodochrous* strain NCIMB 41164 which is described and claimed in our co-filed UK patent application 0327907.2 which has been allocated case reference number BT/3-22351/P1.

*Rhodococcus rhodochrous* strain NCIMB 41164
1. Origin and Deposition

The strain NCIMB 41164 was isolated by us from soil in Bradford, England and deposited on 5 Mar. 2003 at the National Collection of Industrial and Marine Bacteria (NCIMB), where it was assigned the accession number NCIMB 41164 under the Budapest Treaty.

The current address of the depository collection NCIMB is
NCIMB Ltd.
Ferguson Building
Crabstone Estate
Bucksburn, Aberdeen
Scotland, AB219YA 2. Morphological and cultural characteristics
    (1) Polymorphic growth
    (2) Motility: immotile
    (3) Non-spore former
    (4) Gram positive
    (5) Aerobic
    (6) Growth on nutrient agar gives salmon pink round colonies within 48 hours at 30° C.

A particularly advantageous feature of this aspect of the invention is that it is no longer necessary to separate the biocatalyst from the fermentation mixture in which it was cultured. This is of significant value since it avoids the requirement for an additional processing step. Therefore the composition may also comprise a fermentation mixture, which is then stored. In the method of storing the biocatalyst, we find that this may also be achieved in the presence of a fermentation mixture without any detrimental effects on the activity of the enzyme. This then allows the fermentation broth to be used immediately to catalyse the reaction, or to allow it to be stored for several days or even weeks without detriment whilst the bioconversion step is being carried out also over a period of several days, thus ensuring a constant supply of readily available biocatalyst without need for additional processing steps thus simplifying and reducing the cost of the bioconversion step.

The biocatalyst may conveniently be stored at temperatures above its freezing point. Typically the biocatalyst may be stored at ambient temperatures, for instance up to 30 or 40° C. However, the advantage of the present method is that the biocatalyst may be stored at ambient temperatures without any special precautions for monitoring and controlling the temperature. Preferably the biocatalyst is stored at a temperature between 4 and 30 or 40° C., more preferably between 5 and 25° C., such as between 10 and 25° C. and in particular 15 to 25° C.

In accordance with the invention the biocatalyst may have been held in an environment containing oxygen or held in an oxygen-free environment. It may or may not contain residual fermentation broth components prior to commencing the conversion of the nitrile. This may be as a result of storing the biocatalyst in accordance with the storage of the microorganism in the presence of the fermentation broth components.

As given previously the biocatalyst does not need to be removed from the fermentation mixture in which the biocatalyst has been prepared. In accordance with the present invention the environment in which the biocatalyst is held also contains components of a fermentation broth. Therefore a biocatalyst composition containing components of a fermentation broth can be combined with a nitrile which is then hydrated to the corresponding amide. We have found surprisingly that in contrast to previous knowledge; for instance in U.S. Pat. No. 5,567,608, which states that immobilisation of the biocatalyst is preferable to prevent elution of impurities from the biocatalyst into the reaction product, that the inclusion of fermentation broth in the reaction mixture does not affect the quality of the final product and this aspect is described in our co-filed UK application 0327901.5, identified by case number BT/3-22349/P1.

The fermentation mixture will comprise essential components for allowing microorganisms to be grown and sustained. In general the mixture will at least contain a carbon source, nitrogen source and various nutrients. This may include a saccharide for instance a monosaccharide such as glucose or other sugar or a disaccharide or polysaccharide, ammonium salts, complex medium components such as yeast extract and peptone, amino acids, vitamins, phosphate salts, potassium, sodium, magnesium and calcium salts, trace elements such as iron, cobalt, manganese, copper, zinc and the like. These and other ingredients can be included in the fermentation mixture at concentrations suitable for the particular microorganism. It is known that fermentations can be subject to changes in the productivity of the biocatalyst and the fermentation broth may be used at different stages of growth and so it is important to be able to store the biocatalyst after production in such a way.

We find that the activity of the biocatalyst does not diminish significantly during the reaction for a prolonged period. Consequently the biocatalyst may be replaced less frequently. Preferably the biocatalyst is used for a period of at least 2 days and loses substantially no activity over that period.

Generally the catalysis of the reaction using nitrile hydratase enables the nitrile to be converted into the corresponding amide in a single step. This process is of particular value when the nitrile is acrylonitrile and the amide is acrylamide. It is desirable to carry out this conversion step several times using a single batch of biocatalyst from which portions are removed over a period of several days to carry out several reactions where nitrile is converted to amide. Thus, it is important to be able to store the biocatalyst as inexpensively as possible without detriment to the catalyst whilst the bioconversion step is carried out simultaneously. So in effect one batch of biocatalyst can be stored ready for use to make several batches of for instance acrylamide. Several batches could be from 5 to 10 or more batches, even 15 to 20 batches.

The following examples are an illustration of the invention.

EXAMPLE 1

(1)*Rhodococcus rhodochrous* NCIMB 41164 was grown in a 280 L fermenter containing 180 L culture medium containing the following constituents (g/L): dipotassium hydrogen phosphate 0.7; Potassium hydrogen phosphate 0.3; glucose 1.0; yeast extract 3.0; magnesium sulphate heptahydrate 0.5; cobalt chloride hexahydrate 0.01; urea, 5.0. The pH of the medium was adjusted to pH 7.2. The culture was grown at 30° C. for 3 days.

25 L of the fermentation broth was degassed with nitrogen for 20 minutes prior to storage at ambient temperature, which was approx. 5° C. for 3½ days. The nitrile hydratase activity was measured 15 h after harvesting and it was found to be 242,000 U/g at 25° C. When the NH activity was re-measured immediately prior to the first acrylamide production trial 3 days later it was found to be 293,000 U/g.

EXAMPLE 2

*Rhodococcus rhodochrous* NCIMB 41164 was grown in a 2 L Erlenmeyer flask for 5 days at 28OC with shaking at 180 rpm in a culture medium containing the following constituents in g/L: diPotassium hydrogen phosphate 0.7; Potassium hydrogen phosphate 0.3; glucose 10.0; yeast extract 3.0; urea 5.0; magnesium sulphate heptahydrate 0.5; cobalt chloride hexahydrate 0.01. The bacterial cells from half of the culture broth were harvested using centrifugation. The culture broth was divided into two portions, one half of which was deoxygenated using nitrogen for 10 minutes. Portions of both the deoxygenated and the oxygenated culture broth were incubated at 4, 15 and 25° C. for 1 week. The nitrile hydratase activity of the portions was measured periodically.

The results of the nitrile hydratase assays are shown in Table 1. The results are given in U/mg dry cells

TABLE 1

| Incubation temp. | Time (days) | | | | | |
|---|---|---|---|---|---|---|
| | 0 | 1 | 2 | 3 | 5 | 7 |
| 4° C. (O2) | 140 | 286 | | 232 | 267 | 257 |
| 4° C. (degassed) | | 274 | | | 214 | 293 |
| 15° C. (O2) | | | | | | |
| 15° C. (degassed) | 140 | 218 | | | | |
| 25° C. (O2) | 140 | 143 | | | | |
| 25° C. (degassed) | | 154 | 230 | | | |

EXAMPLE 3

*Rhodococcus rhodochrous* J1 was grown in a 2 L Erlenmeyer flask for 5 days at 28° C. with shaking at 180 rpm in a culture medium containing the following constituents in g/L: dipotassium hydrogen phosphate 0.5; Potassium hydrogen phosphate 0.5; glucose 20.0; peptone, 5.0; yeast extract 1.0; urea 7.5; magnesium sulphate heptahydrate 0.5; cobalt chloride hexahydrate 0.01. The bacterial cells from half of the culture broth were harvested using centrifugation. The culture broth was divided into two portions, one half of which was deoxygenated using nitrogen for 10 minutes. Portions of both the deoxygenated and the oxygenated culture broth were incubated at 4, 15 and 25° C. for 1 week. The nitrile hydratase activity of the portions was measured periodically. The results are shown in Table 2.

TABLE 2

| Incubation temp. | Time (days) | | | | | |
|---|---|---|---|---|---|---|
| | 0 | 1 | 2 | 3 | 5 | 7 |
| 4° C. (O2) | 78 | 86 | | | 87 | 78 |
| 4° C. (degassed) | | 92 | | 101 | 90 | 73 |
| 15° C. (O2) | | | | | | |

TABLE 2-continued

| Incubation temp. | Time (days) | | | | | |
|---|---|---|---|---|---|---|
| | 0 | 1 | 2 | 3 | 5 | 7 |
| 15° C. (degassed) | 78 | 94 | | | | |
| 25° C. (O2) | 78 | 96 | | | | |
| 25° C. (degassed) | | 90 | 86 | | | |

It can be seen from the results of both Examples 2 and 3 and that the biocatalyst can be stored effectively at ambient temperatures. Furthermore it can be seen that the nitrile hydratase activity does increase on storage by comparison to day zero. This was most noticeable for *Rhodococcus rhodochrous* NCIMB 41164.

EXAMPLE 4

Defrosted cells of *Rhodococcus rhodochrous* NCIMB 41164 were resuspended in water. The nitrile hydratase activity was measured over a period of 1 week. The relative nitrile hydratase activites measured are shown in Table 3.

TABLE 3

| Time (days) | Relative nitrile hydratase activity (%) | | |
|---|---|---|---|
| | 4° C. | 15° C. | 25° C. |
| 0 | 100 | 100 | 100 |
| 1 | 66 | 64 | 66 |
| 2 | 78 | 77 | 76 |
| 5 | 72 | 72 | 74 |
| 7 | 68 | 74 | 73 |

The results in Table 3 show that the activity did not decrease at any of the temperatures of storage between the 1 and 7 day incubation period.

EXAMPLE 5

(1) *Rhodococcus rhodochrous* NCIMB 41164 was grown in a 0.5 L baffled Erlenmeyer flask containing 100 mL culture medium containing the following constituents (g/L): diPotassium hydrogen phosphate 0.7; Potassium hydrogen phosphate 0.3; glucose 10.0; yeast extract 3.0; magnesium sulphate heptahydrate 0.5; Urea 5.0; cobalt chloride hexahydrate 0.01; tap water to 1 L. The pH of the medium was adjusted to pH 7.2. The culture was grown at 30° C for 4 days. The nitrile hydratase activity was measured at 25° C. after 2,3 and 4 days growth.

(2) (a) *Rhodococcus rhodochrous* NCIMB 41164 was grown in the medium described in (1) except that the urea was replaced by dimethylurea.

(b) *Rhodococcus rhodochrous* NCIMB 41164 was grown in the medium described in (1) except that the urea was replaced by ethylurea.

(c) *Rhodococcus rhodochrous* NCIMB 41164 was grown in the medium described in (1) except that 2.5 g/l urea and 2.5 g/l dimethylurea were added to the medium in place of the 5 g/l urea.

(d) *Rhodococcus rhodochrous* NCIMB 41164 was grown in the medium described in (1) except that 2.5 g/l urea and 2.5 g/l ethylurea were added in place of the 5 g/l urea.

The nitrile hydratase activities are shown in Table 4.

TABLE 4

| Urea compound | Nitrile hydratase activity (μmol/min/g dry cells) | | |
|---|---|---|---|
| | 2 days | 3 days | 4 days |
| urea | 6,800 | 34,800 | 123,200 |
| Dimethylurea | 14,600 | 73,800 | 97,600 |
| Ethylurea | 14,500 | 110,100 | not determined. |
| Urea + dimethylurea | 7,400 | 27,000 | 19,400 |
| Urea + ethylurea | 6,000 | 6,900 | 73,850 |

The invention claimed is:

1. A method of producing an amide from the corresponding nitrile comprising the following steps,
   i) providing a microorganism capable of producing a nitrile hydratase biocatalyst,
   ii) culturing the microorganism in a growth medium,
   iii) storing the microorganism in a storage medium that comprises water and the growth medium in step ii),
   iv) contacting the nitrile with the microorganism in the storage medium of step iii) without recovery of the microorganism using centrifugation or filtration and thereby converting the nitrile to the amide,
wherein the microorganism is stored in step iii) as a non-actively growing culture in the storage medium and the term non-actively growing culture means that the metabolism in the microorganism cells is substantially zero and the microorganism is Rhodococcus rhodochrous NCIMB 41164.

2. A method according to claim 1 in which the amide is an ethylenically unsaturated amide.

3. A method according to claim 1 in which the growth medium comprised in the storage medium of step iii) comprises urea or a urea derivative.

4. A method according to claim 1 in which the microorganism is stored at a temperature above the freezing point of the storage medium.

5. A method according to claim 1 in which the microorganism is stored for a period of at least 2 days.

\* \* \* \* \*